(12) United States Patent
McAuliffe

(10) Patent No.: US 6,903,360 B2
(45) Date of Patent: Jun. 7, 2005

(54) METHOD FOR DETECTING MISSING COMPONENTS AT ELECTRICAL BOARD TEST USING OPTOELECTRONIC FIXTURE-MOUNTED SENSORS

(75) Inventor: Robert E. McAuliffe, Loveland, CO (US)

(73) Assignee: Agilent Technologies, Inc., Palo Alto, CA (US)

(*) Notice: Subject to any disclaimer, the term of this patent is extended or adjusted under 35 U.S.C. 154(b) by 258 days.

(21) Appl. No.: 10/272,113

(22) Filed: Oct. 16, 2002

(65) Prior Publication Data

US 2004/0075067 A1 Apr. 22, 2004

(51) Int. Cl.[7] .......................... G01N 21/88; G01V 8/00
(52) U.S. Cl. ............................ 250/559.4; 250/559.44; 356/237.3; 324/537
(58) Field of Search ...................... 250/559.4, 559.44, 250/559.45; 356/237.3–237.5

(56) References Cited

U.S. PATENT DOCUMENTS 5,006,808 A * 4/1991 Watts ........................ 324/537
5,124,660 A * 6/1992 Cilingiroglu ................ 324/538
5,138,266 A * 8/1992 Stearns ....................... 324/537
5,254,953 A   10/1993 Crook et al.

FOREIGN PATENT DOCUMENTS

JP      02061505 A      8/1988
JP      04348210 A      12/1992

* cited by examiner

Primary Examiner—Stephone B. Allen

(57) ABSTRACT

Disclosed is a method and apparatus for determining the presence or absence of a component on a printed circuit board. The method and apparatus utilizes a photo-sensor and photo-detector that are positioned within a predetermined non-contacting distance from the expected location of a given component under test. The photo-emitter emits a controlled amount of light energy on the expected location of the component under test on the printed circuit board. The photo-sensor detects the amount of reflection off the surface of the expected location of the component under test. Because the amount of reflection differs between reflection off the surface of the component under test and reflection off the surface of the bare board, based on the reflection measurement, the component under test can be classified as either present or absent at its expected location on the printed circuit board.

14 Claims, 5 Drawing Sheets

METHOD FOR DETECTING MISSING COMPONENTS AT ELECTRICAL BOARD TEST USING OPTOELECTRONIC FIXTURE-MOUNTED SENSORS

FIELD OF THE INVENTION

The present invention relates, in general, to electrical board testing, and more particularly to a novel method and apparatus for detecting missing components from a printed circuit board.

BACKGROUND OF THE INVENTION

Electronic products are physically decreasing in size at a rapid rate. At the same time, consumers have become more demanding in their expectations of the quality and reliability of the products they buy. In order to meet quality requirements, electronic product manufacturers must thoroughly test the product at various stages during the manufacturing process. However, as electronic devices become smaller, access to the critical portions (e.g., electrical circuit nodes) of the device necessary for testing the product has become more and more difficult. This problem is occurring in a time when many manufacturers are also facing an increasing need to test product components faster and more efficiently.

A printed circuit board (PCB) is subject to many different types of defects during the assembly process. Accordingly, various test and inspection techniques are employed to locate these defects. Today, there are three general test methods used to find PCB defects: electrical test, optical (or visual) inspection, and x-ray inspection. Of these, electrical test, and in particular a technique known as "in-circuit test", is the most mature and most commonly used technique. However, as physical access to nodes on the PCB via bed-of-nails probing decreases, in-circuit test is becoming less effective.

One of the most prevalent defects on PCB assemblies today is missing devices. The devices are either never loaded onto the board or they fall off during the assembly process. Prior methods for detecting missing devices at the electrical test stage of the process include in-circuit test, functional test, capacitive measurement test, scan test, automated optical test, and automated x-ray test.

In-circuit test, including unpowered in-circuit analog test (for discrete analog components) and digital in-circuit test for digital components, utilizes an in-circuit tester. The in-circuit tester includes a bed-of-nails test-head having a number of tester interface pins. A fixture having a number of probes is mounted over the bed-of-nails of the tester such that the fixture probes align with and contact tester interface pins. A printed circuit board under test is mounted in the fixture such that the fixture probes electrically contact various nodes of interest on the PCB under test. Analog in-circuit tests detect missing components on the PCB under test by probing the appropriate nodes to which the component under test should be attached, and measuring the value, in appropriate units (e.g., resistance, capacitance, etc.), of the component under test. If the measured value is within predetermined limits of the expected value, the test infers that the component under test is indeed present.

Similarly, in functional test, input and output nodes on the board to which the component under test should be attached are probed, digital values are applied to the input nodes, and digital results are collected from the output nodes. If the correct results are collected, the test infers that the component under test is indeed present.

Capacitive measurement test, such as Agilent Technology's TestJet™ probe and technique (described in detail in U.S. Pat. No. 5,254,953 to Crook et al., and incorporated herein by reference for all that it teaches), detects when a device pin is not properly connected to its trace on the PCB. The technique uses an external plate, suspended over the device under test and separated from the lead frame by the plastic or ceramic material of the device housing The lead frame and external plate form a small capacitor that can be measured by stimulation with an AC source. When the device pin is not electrically connected to the trace, an additional capacitance results in series with the TestJet™ capacitor. This additional capacitance exists due to the tiny air gap between the pin and trace. This is a very small capacitance, much smaller than the TestJet™ capacitor, so the series combination of the TestJet™ and this additional pin capacitor is smaller than either capacitor. A threshold value can be set for each pin of each device under test to discriminate between present and absent devices.

Missing digital devices can often be detected using scan test methodologies based on IEEE 1149.1. However, scan test only works on devices that conform to the IEEE 1149.1 standard. Furthermore, even scan test requires some probing. Moreover, the absence of certain classes of devices connected in difficult topologies cannot be detected by electrical methods even if physical probing is provided. Parallel bypass capacitors are one example.

Another emerging technique for detecting missing devices on a PCB is through mechanical switching detection. In this technique, a spring-loaded probe attempts to probe a part where it should be located. If the part is present, the spring of the probe compresses to close a mechanical switch, which completes a circuit to allow current to flow. Thus, when the device is present, current is measurable in the circuit; likewise, when the device is not present, no current flows through the circuit. The mechanical switching detection technique is problematic in that it contains moving parts, making it susceptible to part failure, and requires physical contact of the component under test.

The above techniques each require at least some physical probing of the PCB nodes (with the exception of the mechanical switching technique) and are therefore ineffective for PCB assemblies with limited nodal access. To overcome loss of test coverage in non-probed areas of the PCB, alternate test methodologies have emerged. These include automated optical inspection (AOI) and automated x-ray inspection (AXI). Although these methodologies can detect missing devices very effectively, they each suffer from their own limitation and disadvantages. The major disadvantage of these techniques is that they require expensive manufacturing line equipment entirely separate from the in-circuit tester, and therefore also require an entirely new test step to be added to the manufacturing process. The cost of adding such machines to the manufacturing process may be appropriate in some cases, but in other cases the need to do so represents a large disadvantage to these methods.

Since most manufacturing lines already use electrical testers (primarily in-circuit testers), it would be beneficial to have the ability to detect missing devices during the in-circuit stage of the manufacturing process. However, due to decreased access to PCB nodes due to ever-decreasing node spacing, the current solutions for detecting missing devices on a PCB are becoming less viable. The primary reason for this is that most electrical techniques used today to check for missing components depend on physical access, especially for analog components.

Another force at work decreasing the viability of electrical testers in detecting missing PCB components is that some devices are electrically untestable even with probing. The primary example of this is parallel bypass capacitors. While it is theoretically possible (e.g., on the bench with a single device under test (DUT)) to detect a single missing capacitor, in practice such detection is often not possible. The tolerances and guardbands that must be added to the test limits completely hide small measurement differences due to a single (or even multiple) missing capacitors. As MSI and LSI are replaced by VLSI components, FPGAs and large ASICs, the ratio of bypass capacitors to digital components is increasing, which decreases the number of possible faults that are detectable by even a perfect electrical test.

Accordingly, it is an object of the invention to detect missing components on a PCB while the PCB is being electrically tested on an in-circuit tester.

It is also an object of the invention to detect missing components without physically probing the circuit.

It is yet another object of the invention to detect missing components that currently may not be detected by any prior art electrical test method in a manufacturing environment.

SUMMARY OF THE INVENTION

The present invention provides a solution to the above problems and offers the ability to detect missing components (including bypass capacitors) at the in-circuit test stage of the manufacturing process using non-electrical methods. The component detection apparatus of the invention employs subminiature reflective object sensors which integrate an infrared (IR) emitter and detector in the same package. The emitter and detector are optically aligned to detect reflective surfaces at distances of about 1 to 5 mm. By positioning the component detection apparatus directly above a component under test (such as bypass capacitor), it is possible to detect a difference in reflection, which indicates the presence or absence of the component.

The present invention is advantageous over the prior art for several reasons. In contrast to analog in-circuit testing, the present invention detects missing devices without the need for physical probes and without knowledge of the circuit topology. Furthermore, the invention is not affected by the circuit topology.

In contrast to digital in-circuit testing, the present invention detects missing devices with no digital test programming, without the need for physical probes, and without knowledge of the circuit topology. Furthermore, the invention is not affected by the circuit topology.

In contrast to Agilent Technology's TestJet™ technology, the present invention detects missing devices without the need for physical probes and does not depend on sensitive analog measurements.

In contrast to scan-based digital test, the present invention works on devices that do not comply to the IEEE 1149.1 standard.

In contrast to testing via the mechanical switch technique, the present invention does not use moving parts and requires no mechanical contact.

In contrast to automated optical inspection (AOI), the present invention does not require a separate tester or test step in the manufacturing process and is much less expensive.

In contrast to automated x-ray inspection (AXI), the present invention does not require a separate tester or test step in the manufacturing process and is much less expensive.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein.

DETAILED DESCRIPTION

A novel method and apparatus for determining the presence or absence of a component on a printed circuit board is described in detail hereinafter. Although the invention is described in terms of specific illustrative embodiments, it is to be understood that the embodiments described herein are by way of example only and that the scope of the invention is not intended to be limited thereby.

Figure 1A:
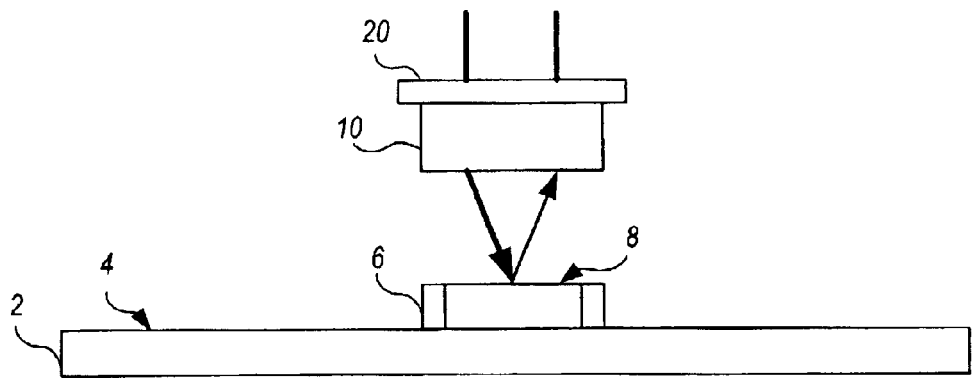
FIG. 1A is a profile view of a printed circuit board under test with a component under test present which illustrates the method and apparatus for component detection.
Figure 1B:
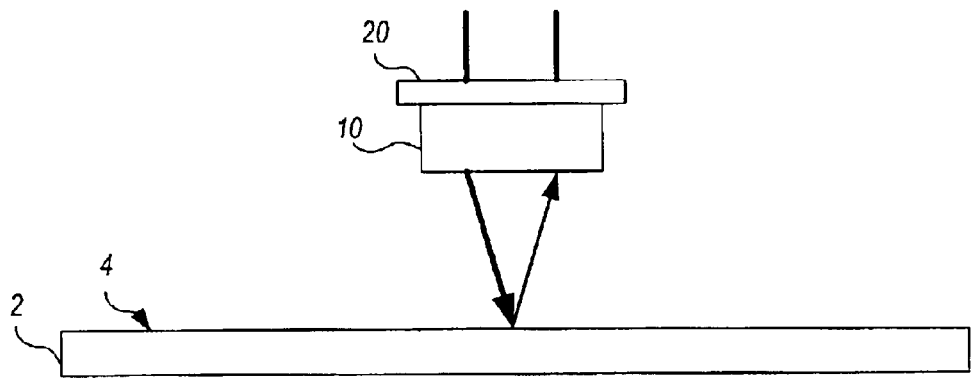
FIG. 1B is a profile view of the printed circuit board under test of FIG. 1A with the component under test absent which illustrates the method and apparatus for component non-detection.

Turning now to the invention, FIGS. 1A and 1B illustrate a printed circuit board under test 2 having a first surface 4 on which a circuit component 6 is expected to be mounted. A component detector 10 is positioned in close but non-contacting proximity to the location where the component under test 6 is expected to be attached. The component detector 10 emits light energy (preferably in the infrared (IR) range) in the direction of the expected location of the component under test 6 and senses the reflectivity of the emitted light off the surface of either the component under test 6 (when the component 6 is present) or bare printed circuit board 2 (when the component under test 6 is not present). A combination of the difference in distances between the surface 8 of the component under test 6, when present, and the surface 4 of the board 2, when the component under test 6 is not present, and the potentially different reflectivity constants of the surfaces 4 and 8, result in two different reflectivity measurements depending on whether the component under test 6 is present or absent.

FIG. 1A illustrates the case where the component under test 6 is present on the board 2. In this case, the IR energy emitted from the component detector 10 reflects off the top surface 8 of the component under test, resulting in a first reflectivity $R_C$.

FIG. 1B illustrates the case where the component under test 6 is not present on the board 2. In this case, the IR energy emitted from the component detector 10 reflects off the surface 4 of the board 2, resulting in a second reflectivity $R_B$, which is different than the first reflectivity $R_C$.

Depending on whether the component 6 is present or missing from the board 2, two parameters may affect the reflectance $R_C$ or $R_B$: the distance between the sensor 14 (FIG. 2) in the component detector 10 and the reflective surface 4 or 8, and the reflectivity constants of the board surface 4 and component surface 8 respectively. Depending on the situation, either of these parameters may contribute more dominantly to the measured reflectance $R_C$ or $R_B$. In most simple cases, the dominant contribution to the measured reflectance $R_C$ or $R_B$ is due to the difference in reflectivity constants of the board surface 4 and component surface 8. In practice, however, the parameter that more dominantly to the measured reflectance $R_C$ or $R_B$ is unimportant so long as a discernable difference in measured reflectivity exists between the cases of component present (e.g., $R_C$) and component absent (e.g., $R_C \pm \text{tolerance} \neq R_B \pm \text{tolerance}$).

Figure 2:
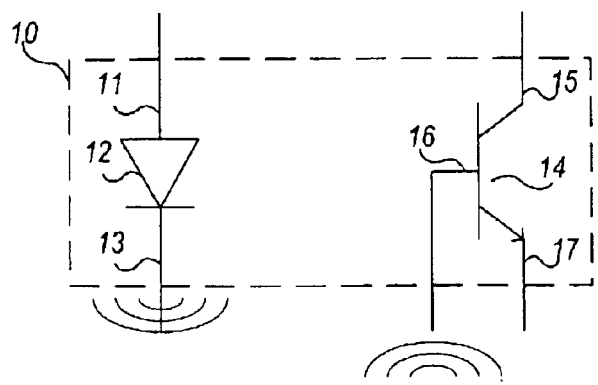
FIG. 2 is a schematic block diagram of a component detector implemented in accordance with a preferred embodiment of the invention.

FIG. 2 is a schematic block diagram illustrating a preferred embodiment of the component detector 10. As illustrated, the component detector 10 includes a photo-emitter 12 and photo-sensor 14. A digital driver 32 (see FIG. 3) drives the anode 11 of the photo-emitter 12, which emits infrared energy. The photo-sensor 14 is preferably a phototransistor connected to a digital receiver 33 in the tester (see FIG. 3), where the gate 16 of the phototransistor operates as the input of the sensor 14.

Figure 3:
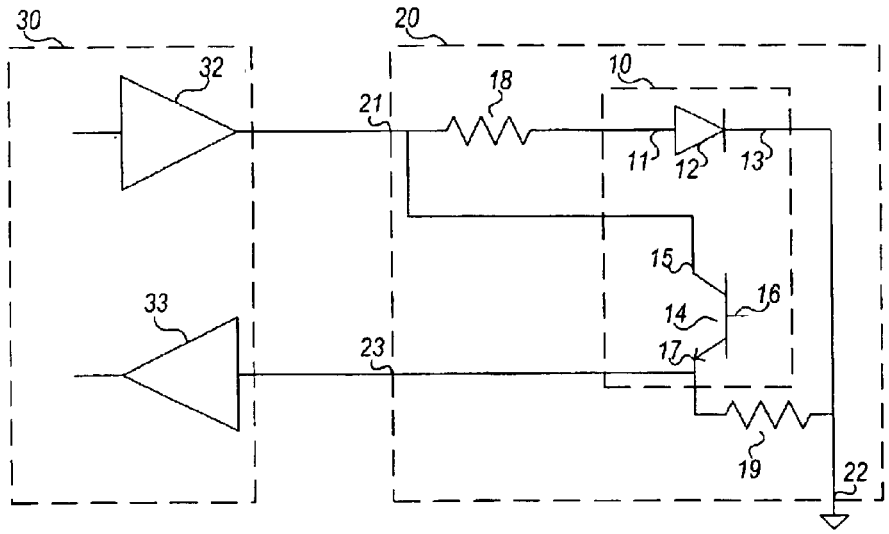
FIG. 3 is a schematic block diagram of a component detection apparatus implemented in accordance with a preferred embodiment of the invention.

FIG. 3 is a schematic diagram of a preferred embodiment of the component detection apparatus 20 of the invention. The apparatus 20 includes an input node 21, an output node 23, and a ground node 22. As illustrated, a digital driver 32 is connected to input node 21 of the component detection apparatus 20 to drive the anode 11 of the photo-emitter 12 through a series resistor 18. The collector of the phototransistor 14, also connected to the input node 21 of the apparatus, is driven by the digital driver 32 of the tester 30 to avoid the need to wire the component detector 10 to any power supplies. The cathode 13 of the photo-emitter 12 and the emitter 17 of the phototransistor 14 (through a resistor 19) are both tied to ground at node 22. The emitter 17 of the phototransistor 14 is connected to the output node 23 of the component detection apparatus 20, which may be connected to a digital receiver 33. The digital driver 32 and receiver 34 may be located in the tester 30 or test fixture 40, or may even be co-located with the component detection apparatus 20 in the same package. Light reflected off the surface of the component under test 6 or bare board 4 is sensed at the gate 16 of the phototransistor 14 which determines the amount of current seen at the emitter 17 of the phototransistor 14.

In the preferred embodiment, the component detector 10 is implemented using a reflective sensor such as the OPTEK SMD Reflective Sensor Type OPR5005, which integrates a photo-emitting diode (specifically a GaAlAs LED) and a phototransistor in a 2.9×4.5 mm surface mount opaque package. The current supplied to the anode 11 of the photo-emitting diode is on the order of 50 mA. The opaque package allows very low cross talk and shields the phototransistor 14 from ambient light sources.

Figure 4:
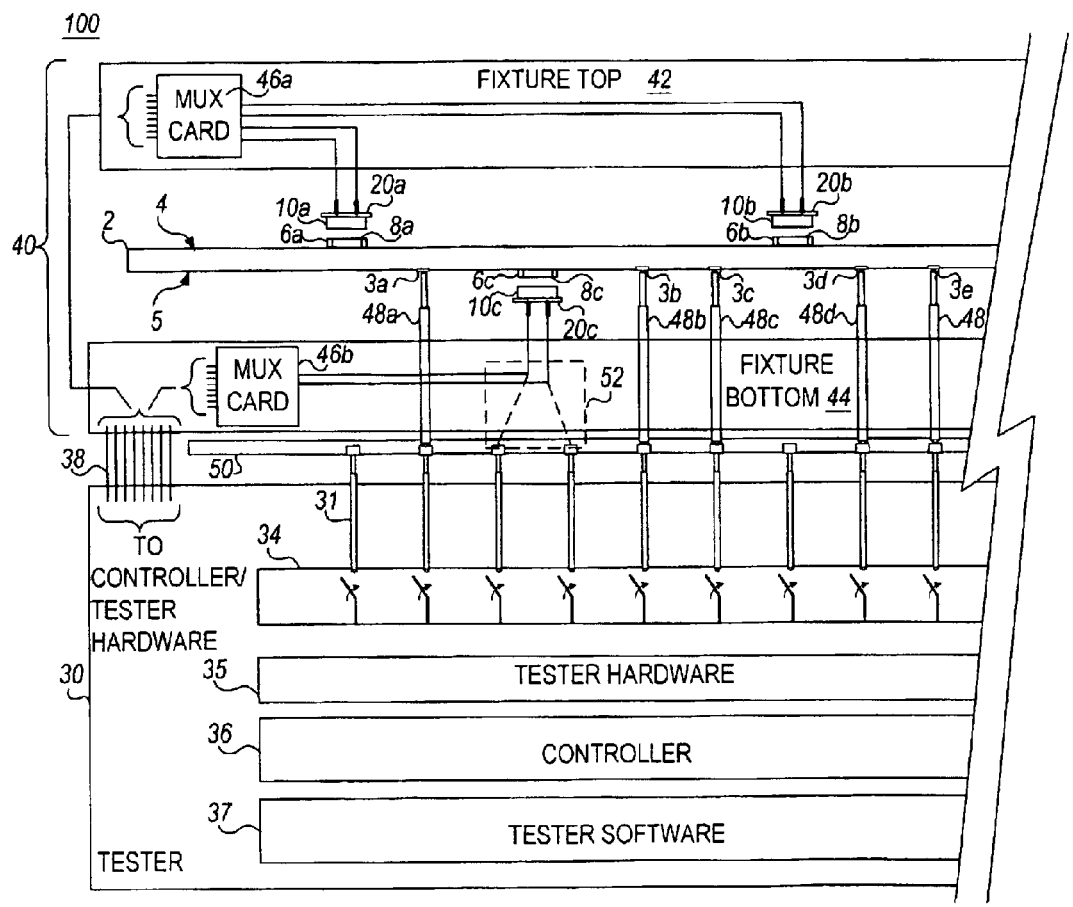
FIG. 4 is a block diagram of an in-circuit tester employing the component detection apparatus of the invention.

Turning now to FIG. 4, there is shown a portion of an in-circuit test system 100 employing several component detection apparatuses 20a, 20b, 20c implemented in accordance with the invention. As illustrated, the in-circuit test system 100 includes a tester 30, a fixture 40, and a PCB under test 2. Due to the close spacing of the tester interface pins, nodes of the PCB under test, and small size of the components under test, only a small edge portion of the tester is shown for ease of illustration.

Tester 20 includes a plurality of tester interface pins 31 arranged in an array (or "bed-of-nails") along the top side of the tester 30. Tester 30 includes tester hardware 35 which operates under the control of a controller 36. Controller 36 may be controlled by tester software 37, which may execute within the tester 30 itself, or remotely via a standard communication interface. One function of the controller 36 is to configure the hardware 35 to make or not make electrical connections between measurement circuits within the tester and each of the test interface pins 31. To this end, each test interface pin 31 is connectable to or isolated from the tester hardware by a relay 34. Electrical contact between the test resources and a respective test interface pin 31 may be made by closing its corresponding relay 34; conversely, the pin 31 may be isolated from the test hardware by opening its corresponding relay 34.

Mounted on top of the tester 30 and over the bed-of-nails test interface pins 31 is the test fixture 40. The test fixture 40 may directly interface the test interface pins 31 to fixture probes 48, or as shown, may indirectly interface the test interface pins 31 to fixture probes 48 through a test adapter 50. The fixture 40 is mounted over the tester interface pins 31 of the tester 30 such that the bottom tips of its double-ended spring probes 48 make electrical contact with the top tips of corresponding test interface pins 31 of the tester 30, either directly, or through a test adapter 50 as shown. The top tips of the double-ended spring probes 48 align with and make electrical contact with conductive pads of interest 3a, 3b, 3c, 3d, 3e on the bottom side of the PCB under test 2. The fixture 40, via the fixture probes 48 or the combination of fixture probes 48 and test adapter 50, provides electrical continuity between tester interface pins 31 of the tester 30 and conductive pads of interest 3a, 3b, 3c, 3d, 3e of the PCB under test 2, thereby providing the tester 30 with probing access to the PCB 2 and allowing the tester to perform traditional in-circuit tests on the PCB under test 2. Traditional in-circuit tests may include, for example, analog tests that measure characteristics (e.g., resistance, capacitance, current, etc.) of analog components to verify that the component charactistics are within desired tolerance ranges. In-circuit tests may also include functional tests to determine whether components on the PCB operate according to the design specification for those components or the PCB.

The fixture 40 includes a fixture top 42 and a fixture bottom 44. The fixture bottom 44 includes a plurality of double-ended spring probes 48 that are inserted through precisely aligned holes in the fixture bottom 44. For convenience of illustration and clarity of the invention, only five such double-ended spring probes 48 are shown; however, it will be appreciated by those skilled in the art that a conventional in-circuit tester will typically have thousands of such probes.

The fixture top 42 is configured with a number of component detection apparatuses 20a, 20b, one each corresponding to each component under test 6a, 6b on the top side 4 of the PCB 2 under test. The component detection apparatuses 20a, 20b are mounted to the fixture top 42 such that the component detector 10a, 10b of each apparatus 20a, 20b precisely aligns over its corresponding component under test 6a, 6b within non-contacting but predetermined distance from the expected location of the top surface of the component under test 6a, 6b (if present) when the PCB 2 is properly mounted in the fixture 40.

In the illustrative embodiment, the PCB 2 includes component under tests 6a, 6b, 6c mounted on both sides of the board. Accordingly, accommodation for component detection apparatuses 20 must be made for both sides of the board 2. In this regard, the fixture bottom 44 may also be configured with a number of component detection apparatuses 20c, one each corresponding to each component under test 6c on the bottom side 5 of the PCB 2 under test. The component detection apparatuses 20c are mounted to the fixture bottom 44 such that the component detector 10c of each apparatus 20c precisely aligns beneath its corresponding component under test 6c within non-contacting but predetermined distance from the surface 8c of the component under test 6c (if present) when the PCB 2 is properly mounted in the fixture 40.

In the preferred embodiment, the fixture 40 includes one component detection apparatus 20 for each bypass capacitor, resistor, or other component of interest on the printed circuit board 2. Accordingly, a large number of component detection apparatuses 20 may be required. For this reason, it may be desirable to multiplex the control signals 38 from the tester 30 going to each component detection apparatus 20 to reduce the number of control lines between the tester 30 and fixture 40. In the illustrative embodiment, a single 8-bit multiplexer card 46a, 46b may be used to address up to 256 different component detection apparatuses 20. The multiplexer cards 46a, 46b may also be configured to include the digital driver 32 and receiver 33 (FIG. 3) for each addressable component detection apparatus 20.

Of course, it will be appreciated that the drivers and receivers of each component detection apparatuses 20 may alternatively be wired in a one-to-one correspondence with the tester 30 without the use of multiplexers 46a, 46b, 46c, or other control line reduction schemes. In yet another alternative embodiment, shown at 52, the input 21 and output 23 ports of the component detection apparatuses may be connected to nodes on the fixture, which may be probed by tester interface pins 31. In this alternative configuration 52, the component detection apparatuses may be driven by the tester resources 35 through the tester interface pins 31.

When a component detection test is to be executed, the tester software 37 instructs the tester hardware 35 and/or controller 36 to enable the drivers 32 of the respective component detection apparatuses 20a, 20b, 20c to drive the respective photo-emitters 12 of the respective component detection apparatuses 20a, 20b, 20c to emit a predetermined light energy level. The tester software 37 then instructs the tester hardware 35 and/or controller 36 to enable the receivers 33 of the respective component detection apparatuses 20a, 20b, 20c to receive the sensed light energy level from the photo-transistor 14 due to reflectance of the light emitted by the photo-emitters 12 off of either the surfaces 8a, 8b, 8c of the components under test 6a, 6b, 6c (if present) or the surface 4 of the bare PCB 2 (if the respective component under test 6a, 6b, 6c is not present). The tester hardware 35 and/or controller 36 passes the reflectance results to the tester software 37, which compares the reflectance levels detected by each of the component detection apparatuses 20 to predetermined threshold limit(s) which define whether the component under test is present or absent. Alternatively, the comparison may be performed in hardware. Depending on the wiring configuration of the fixture-to-tester controls, measurements obtained by the component detection test may be taken for each component under test either simultaneously (if the wiring is all done in parallel and the addressing scheme allows it) or may be taken for one or a few components under test at a time.

The predetermined threshold limits may be determined by running a calibration test on a known good board (with all components under test 6a, 6b, 6c known to be present) and on a bare board (or at least where all components under test 6a, 6b, 6c are known to be absent). The results of these calibration tests are used to set the threshold limits (which take into account measurement tolerance levels of the components under test) that discriminate between the presence or absence of a component under test.

Figure 5:
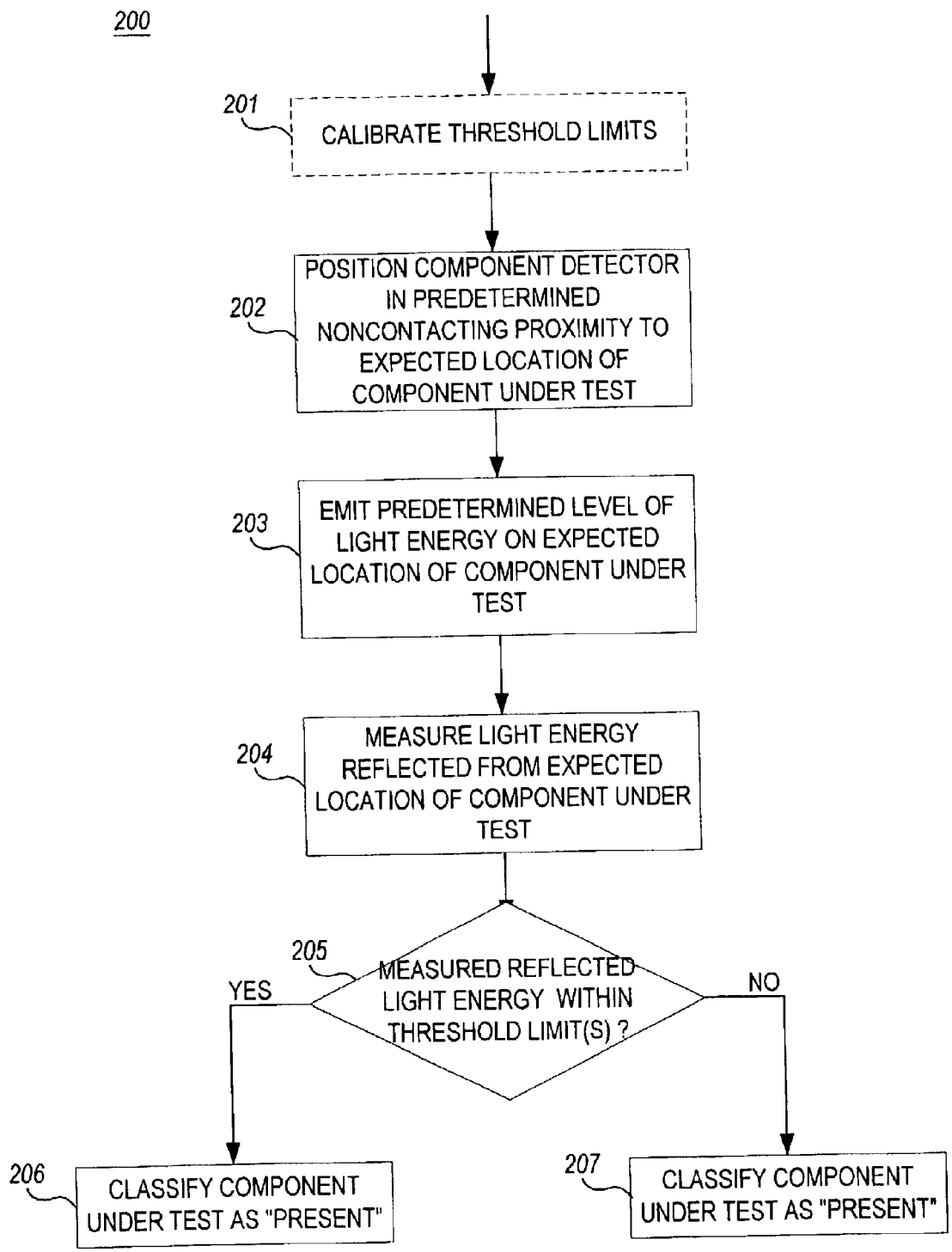
FIG. 5 is an operational flowchart illustrating a component detection method of the invention.

FIG. 5 is a flowchart illustrating an example test for detecting the presence or absence of components under test on a PCB 2. Preferably, the threshold limit(s) which define whether the component under test is present or absent are set and/or determined by calibrating 201 the component detector 10. A preferred method of calibration is discussed with respect to FIG. 6. The calibration step 201 is optional in that the threshold limits may be obtained from manufacturer specifications or from a previous calibration of a similar PCB.

The component detector is positioned 202 in predetermined non-contacting proximity to the expected location designated on the PCB 2 for the component under test 6 such that the emitter 12 and sensor 14 are each positioned within a predetermined non-contacting distance from the expected location of the surface 8 of the component under test 6 when present on the PCB 2.

The emitter 12 emits 203 a predetermined level of light energy in the direction of the expected location of the component under test 6 on the PCB 2.

The sensor 14 senses and measures 204 the light energy reflected off of the surface of either the component under test 6 when present or the surface 4 of the PCB 2 when the component under test 6 is not present.

The measured reflected light energy value is compared 205 to the predetermined threshold limit(s) which define whether the component under test is present or absent.

Based on the comparison in step 205, the component under test 6 is classified as being either present 206 or absent 207 from its expected location on the PCB 2.

In the preferred embodiment test system 100 discussed in FIG. 4, one or more component detection apparatuses 20 are mounted in the tester fixture 40. In this embodiment, the test setup includes a number of component detection apparatuses 20 connected to the tester 30 in parallel. In this case, a single digital test may simultaneously drive all of the component detection apparatuses 20 in parallel, and simultaneously receive the measured results from all the component detection apparatuses 20 in parallel.

In an alternative embodiment, the wiring of the component detection apparatuses 20 is not in parallel, and hence the test (e.g., the method of FIG. 5) must be executed individually for each component detection apparatus 20 (or each group of simultaneously addressable component detection apparatuses 20).

In yet another alternative embodiment, the test setup may include a single component detection apparatus 20 (or small few) positionable by a robotic arm (not shown) under the control of the tester 30. In this alternative embodiment, for each component under test on the PCB, the robotic arm is instructed to be positioned over the respective component under test of interest and the component detection test (FIG. 5) is executed.

Figure 6:
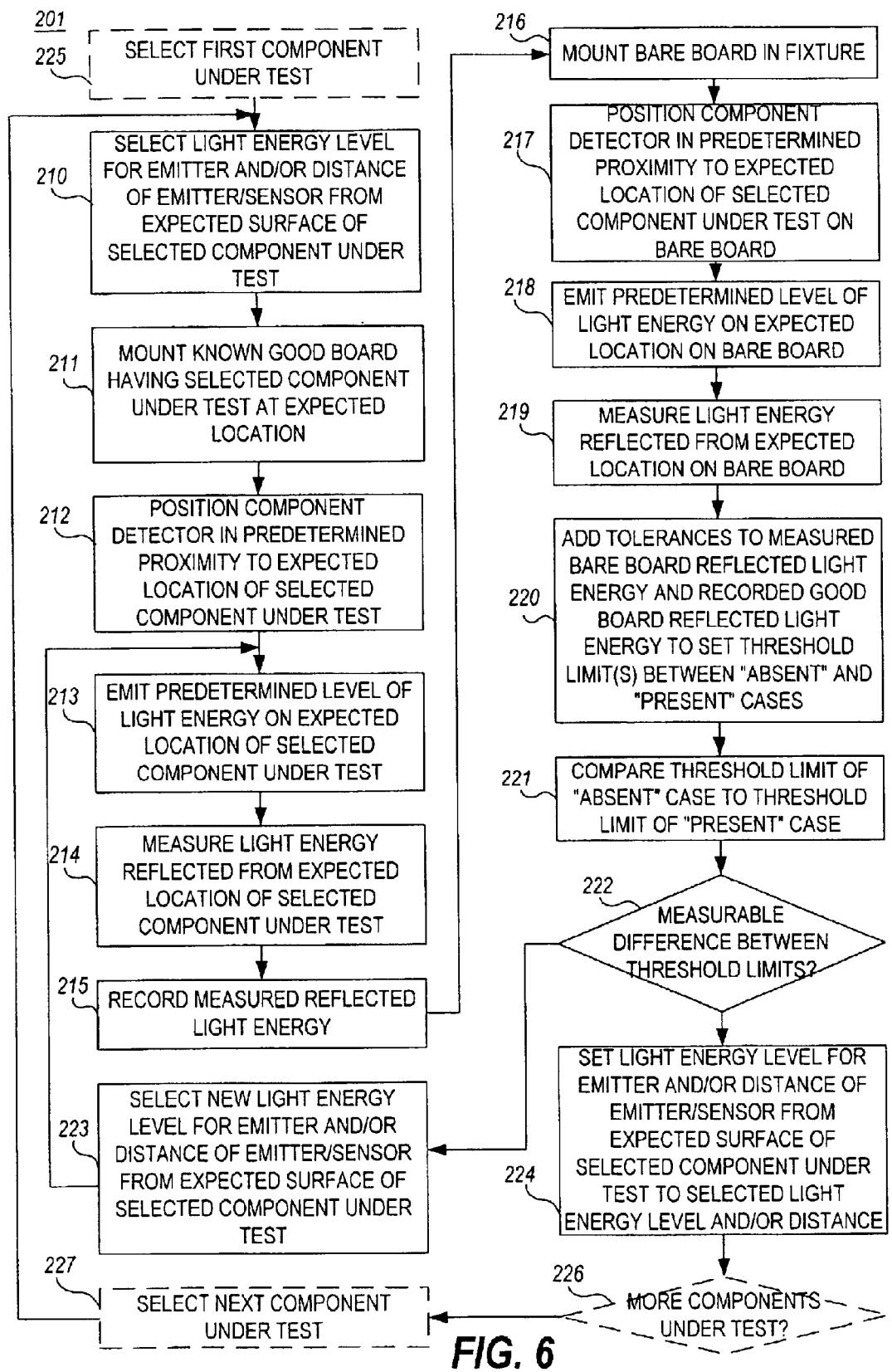
FIG. 6 is an operational flowchart illustrating a preferred embodiment of a component detector calibration method in accordance with the invention.

FIG. 6 is a flowchart illustrating a preferred method for calibrating 201 the component detector and determining the threshold limit(s) which define whether the component under test is present or absent. As illustrated, the calibration method begins by the selection 210 of a light energy level to be emitted by the emitter 12 of the component detector 10 and/or the selection of a distance from which to place the emitter/sensor pair 12/14 from the expected location of the surface 8 of a selected component under test 6.

A known good PCB having components known to be present at the expected locations on the board is then mounted 211 in the fixture. The component detector 10 is positioned 212 at a predetermined proximity to the expected location of the selected component under test 6, and in particular the emitter/sensor pair 12/14 of the component detector 10 is positioned the preselected distance from the expected location of the surface 8 of the selected component under test 6. The emitter 12 emits 213 light energy in the amount of the preselected light energy level on the expected location of the surface 8 of the selected component under test 6. The sensor 14 senses and measures 214 the light energy reflected off the surface 8 of the selected component under test 6. The measured reflected light energy may then be recorded 215.

A bare PCB or one known to have the components under test missing from the expected locations on the board is then mounted 216 in the fixture. The component detector 10 is positioned 217 in predetermined proximity to the expected location of the component under test 6 such that the emitter/sensor pair 12/14 of the component detector 10 is positioned the preselected distance from the expected location of where the surface 8 of the component under test 6 would be if present. The emitter 12 emits 218 light energy in the amount of the preselected light energy level on the expected location of the surface 8 of the selected component under test 6. The sensor 14 senses and measures 219 the light energy reflected off the surface 8 of the selected component under test 6.

Figure 7A:
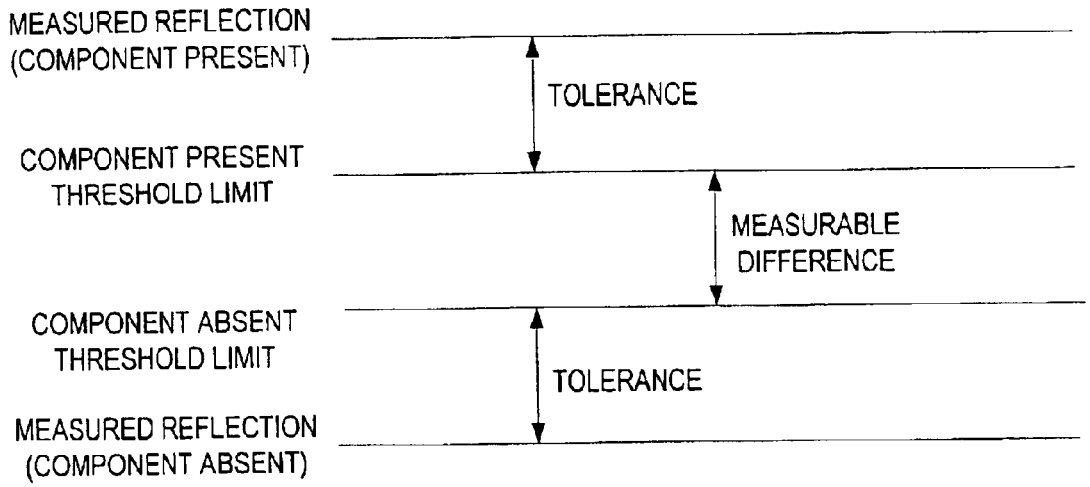
FIG. 7A is a diagram illustrating acceptable reflectance threshold limits.
Figure 7B:
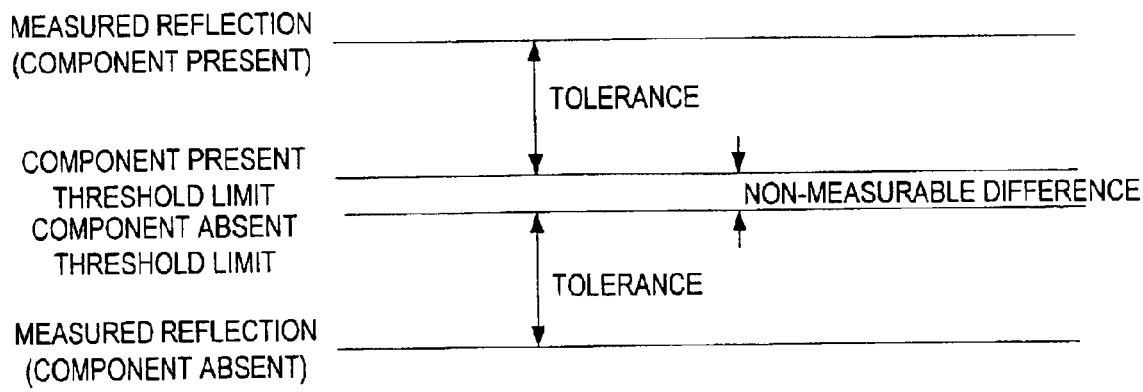
FIG. 7B is a diagram illustrating non-acceptable reflectance threshold limits.
Figure 7C:
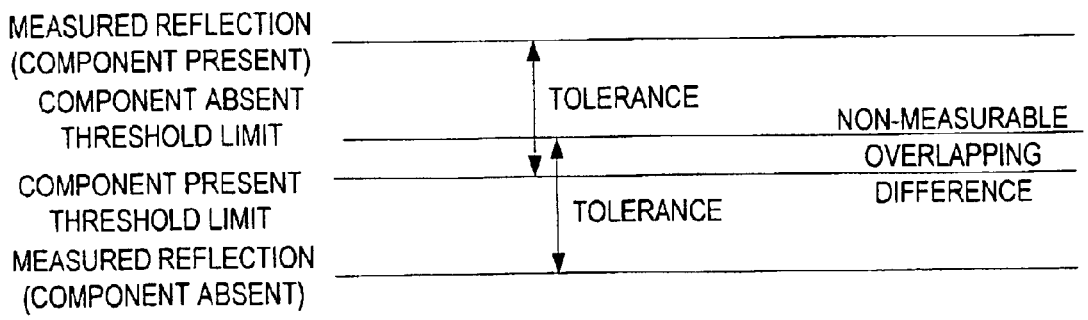
FIG. 7C is a diagram illustrating non-acceptable overlapping reflectance threshold limits.

Tolerances are added 220 to the measured bare board reflected light energy and to the recorded good board reflected light energy (recorded in step 215) to set the threshold limits for the respective component "absent" case and component "present" case. FIGS. 7A–7C illustrate the selection of appropriate threshold limits for distinguishing between the presence or absence of a component under test 6. As illustrated, tolerance limits due to standard measurement errors should be added to the actual measurement for both the known component present case and the known component absent case. The threshold limits will theoretically be set to the actual measurement plus/minus the tolerance and guardband associated with the measurement. Due to the tolerance/guardbands that must be accounted for in the actual measurements for the present and absent cases, it is possible that the values of the threshold limits either do not allow a measurable difference between the present and absent cases (as illustrated in FIG. 7B), or the threshold limits overlap (as illustrated in FIG. 7C). If this is the case, the amount of light energy emitted by the component detector 10 and/or distance between the component detector 10 and expected location of the component under test may have to be adjusted and the calibration test re-executed.

Accordingly, the difference between the threshold limits is compared 221 to determine whether a measurable difference exists 222 between the threshold limits. If so, as illustrated in FIG. 7A, the light energy level of the emitter and/or distance of the emitter/sensor pair from the expected surface of the selected component under test 6 is set 224 to the currently selected light energy level and/or distance. If not, a new light energy level and/or distance of emitter/sensor pair from the expected surface of the component under test 6 is selected 223, and the process is repeated by repeating steps 213 through 222.

The calibration process may be performed on only a single component under test if it is known that all components under test will emit the same amount of reflection and the surfaces of all components under test exist at the same height above the board. However, even for a given component under test part, variations in size or reflection may exist between different manufacturers of the same part. Thus, if it is known that parts from more than one manufacturer of the part will be used on the board, the calibration process should be performed on at least one part from each manufacturer.

In the alternative, the calibration process may be performed for each component under test on the board.

Accordingly, the calibration process 201 may include additional steps. For example, a first component under test may be selected 225 at the beginning of the process 201. Once the light energy level is selected in step 224 for the first component under test, it may be determined in a step 226 whether the calibration method should be performed for additional components under test. If so, another component under test may be selected 227, and the calibration test steps 210 through 224 re-executed. The method may be repeated for additional components under test as needed.

Although this preferred embodiment of the present invention has been disclosed for illustrative purposes, those skilled in the art will appreciate that various modifications, additions and substitutions are possible, without departing from the scope and spirit of the invention as disclosed in the accompanying claims. For example, it should be understood that the component detection apparatus 10 may be implemented with an emitter and detector pair integrated into a single compact package, or may be otherwise embodied so long as it emits energy that is reflected off the surface of the expected location of the component under test and senses the resulting reflection. It is also possible that other benefits or uses of the currently disclosed invention will become apparent over time.

What is claimed is:

1. A method for determining the presence or absence of a component on a printed circuit board, comprising:

placing a photo-emitting diode in non-contacting proximity to an expected location of a component under test on said printed circuit board;

enabling said photo-emitting diode to emit said light energy on said expected location of said component under test on said printed circuit board;

sensing light energy reflected off a surface of said component under test or said printed circuit board at said expected location;

measuring a value corresponding to an amount of said sensed light energy; and classifying said component under test as present or absent based on said value of said sensed light energy.

2. A method in accordance with claim 1, wherein said sensing step comprises:

placing a photo-sensor in non-contacting proximity to said expected location of said component under test on said printed circuit board; and enabling said photo-sensor to sense said reflected light energy.

3. A method in accordance with claim 2, wherein said classifying step comprises:

comparing a value of said sensed reflected light energy to one or more acceptable reflection limits; and indicating that said component is present if said value of said sensed reflected light energy meets said one or more acceptable reflection limits.

4. A method in accordance with claim 1, wherein said classifying step comprises:

comparing a value of said sensed reflected light energy to one or more acceptable reflection limits; and indicating that said component is present if said value of said sensed reflected light energy meets said one or more acceptable reflection limits.

5. An apparatus for detecting a presence or absence of a component on a printed circuit board, comprising:

a photo-emitter which emits light energy on an expected location of said component on said printed circuit board, said photo-emitter positioned in predetermined non-contacting proximity to said expected location of said component under test on said printed circuit board;

a photo-sensor which senses light energy reflected off a surface of said expected location on said printed circuit board, said photo-emitter positioned in predetermined non-contacting proximity to said expected location of said component under test on said printed circuit board, said surface of said expected location comprising a surface of said component under test if said component under test is present at said expected location, and said surface comprising a surface of said printed circuit board if said component under test is absent from said expected location; and a comparator which compares said sensed light energy to one or more reflection threshold limits and indicates whether said component is present or absent.

6. An apparatus in accordance with claim 5, comprising:

a test driver which drives said photo-emitter to emit said light energy on said expected location of said component on said printed circuit board; and a test receiver which enables said photo-emitter to sense said reflected light energy from said surface of said expected location.

7. An apparatus in accordance with claim 6, comprising:

a fixture which seats said printed circuit board and houses said photo-emitter and said photo-sensor in predetermined non-contacting proximity to said expected location of said component under test on said printed circuit board.

8. An apparatus in accordance with claim 6, comprising:

a tester which instructs said test driver to drive said photo-emitter to emit a predetermined amount of said light energy on said expected location, which obtains a sensed reflected light energy measurement from said test receiver, and which comprises said comparator which compares said sensed light energy to one or more reflection threshold limits and indicates whether said component is present or absent.

9. An apparatus in accordance with claim 5, comprising:

a fixture which seats said printed circuit board and houses said photo-emitter and said photo-sensor in predetermined non-contacting proximity to said expected location of said component under test on said printed circuit board.

10. An apparatus in accordance with claim 9, comprising:

a tester which instructs said test driver to drive said photo-emitter to emit a predetermined amount of said light energy on said expected location, which obtains a sensed reflected light energy measurement from said test receiver, and which comprises said comparator which compares said sensed light energy to one or more reflection threshold limits and indicates whether said component is present or absent.

11. An apparatus in accordance with claim 5, comprising:

a tester which instructs said test driver to drive said photo-emitter to emit a predetermined amount of said light energy on said expected location, which obtains a sensed reflected light energy measurement from said test receiver, and which comprises said comparator which compares said sensed light energy to one or more reflection threshold limits and indicates whether said component is present or absent.

12. A fixture for a printed circuit board tester, said printed circuit board tester comprising a plurality of tester interface pins and tester hardware and/or software configurable to drive and/or receive signals on said tester interface pins, said fixture comprising:

a fixture frame;

a printed circuit board mount mounted in said fixture frame which securely seats a printed circuit board under test;

one or more component detection apparatuses, each comprising a photo-emitter and a photo-sensor, and positioned relative to said printed circuit board under test such that said photo-emitter and said photo-sensor of at least one of said component detection apparatuses is positioned at a predetermined non-contacting distance from an expected location of a corresponding component under test on said printed circuit board under test;

wherein each of said at least one of said one or more component detection apparatuses are controllable to drive said photo-emitter to emit light energy on a surface of said expected location of said corresponding component under test and to receive a reflected light energy measurement from said photo-sensor, said surface comprising a surface of said corresponding component under test if said corresponding component under test is present at said expected location and said surface comprising a surface of said printed circuit board under test if said corresponding component under test is absent from said expected location.

13. A fixture in accordance with claim 12, wherein said one or more component detection apparatuses comprises:

at least one component detection apparatus positioned relative to a top side of said printed circuit board under test such that said photo-emitter and said photo-sensor of said at least one of said component detection apparatus is positioned at a predetermined non-contacting distance from an expected location of a corresponding component under test on a top side of said printed circuit board under test; and at least one component detection apparatus positioned relative to a bottom side of said printed circuit board under test such that said photo-emitter and said photo-sensor of said at least one of said component detection apparatus is positioned at a predetermined non-contacting distance from an expected location of a corresponding component under test on a bottom side of said printed circuit board under test.

14. A fixture in accordance with claim 12, wherein said one or more component detection apparatuses comprises a corresponding component detection apparatus for each component under test of interest that exists on the printed circuit board.

* * * * *

UNITED STATES PATENT AND TRADEMARK OFFICE
CERTIFICATE OF CORRECTION

PATENT NO. : 6,903,360 B2
APPLICATION NO. : 10/272113
DATED : June 7, 2005
INVENTOR(S) : McAuliffe Page 1 of 1

It is certified that error appears in the above-identified patent and that said Letters Patent is hereby corrected as shown below:

In column 12, line 17, in Claim 12, after "board" delete "mount".

Signed and Sealed this

Fourteenth Day of November, 2006

JON W. DUDAS
*Director of the United States Patent and Trademark Office*